United States Patent [19]

Magruder et al.

[11] Patent Number: 5,037,420
[45] Date of Patent: Aug. 6, 1991

[54] DELIVERY SYSTEM COMPRISING TWO SECTIONS FOR DELIVERING SOMATOTROPIN

[75] Inventors: Judy A. Magruder, Mt. View; James B. Eckenhoff, Los Altos; Richard Cortese, Los Gatos; Jeremy C. Wright, Los Altos; John R. Peery, Palo Alto, all of Calif.

[73] Assignee: ALZA Corporation, Palo Alto, Calif.

[21] Appl. No.: 513,328

[22] Filed: Apr. 20, 1990

Related U.S. Application Data

[62] Division of Ser. No. 283,359, Dec. 13, 1988.

[51] Int. Cl.⁵ .............................................. A61K 9/22
[52] U.S. Cl. ................................................. 604/892.1
[58] Field of Search ........................ 604/890.1–892.1, 604/27, 48, 49; 424/422, 438

[56] References Cited

U.S. PATENT DOCUMENTS

| | | | |
|---|---|---|---|
| 2,779,241 | 6/1954 | Howard | 89/1 |
| 3,845,761 | 11/1974 | Zaffaroni | 128/130 |
| 3,845,770 | 11/1974 | Theeuwes et al. | 128/260 |
| 3,854,480 | 12/1974 | Zaffaroni | 128/260 |
| 3,865,108 | 2/1975 | Hartop | 128/260 |
| 3,882,233 | 5/1975 | Grant et al. | 514/21 |
| 3,896,819 | 7/1975 | Zaffaroni | 128/130 |
| 3,916,899 | 11/1975 | Theeuwes et al. | 128/260 |
| 3,995,632 | 12/1976 | Nakano et al. | 128/260 |
| 4,002,173 | 1/1977 | Manning et al. | 128/296 |
| 4,063,064 | 12/1977 | Saunders et al. | 219/121 |
| 4,077,407 | 3/1978 | Theeuwes et al. | 128/260 |
| 4,088,864 | 5/1978 | Theeuwes et al. | 219/121 |
| 4,111,202 | 9/1978 | Theeuwes | 128/260 |
| 4,111,203 | 9/1978 | Theuwes | 128/260 |
| 4,160,020 | 1/1979 | Ayer et al. | 424/15 |
| 4,179,337 | 12/1979 | Davis et al. | 424/78 |
| 4,200,098 | 11/1980 | Ayer et al. | 128/260 |
| 4,203,439 | 5/1980 | Theeuwes | 128/260 |
| 4,207,893 | 6/1980 | Michaels | 128/260 |
| 4,235,236 | 2/1980 | Theeuwes | 128/260 |
| 4,285,987 | 8/1981 | Ayer et al. | 427/3 |
| 4,309,996 | 1/1982 | Theeuwes | 128/260 |
| 4,320,759 | 3/1982 | Theeuwes | 128/260 |
| 4,327,725 | 5/1982 | Cortese et al. | 128/260 |
| 4,526,938 | 7/1985 | Churchill et al. | 525/415 |
| 4,599,229 | 7/1986 | Maccecchini | 424/85 |
| 4,612,008 | 9/1986 | Wong et al. | 604/892 |
| 4,652,630 | 3/1987 | Bentle et al. | 530/420.4 |
| 4,765,980 | 8/1988 | DePrince et al. | 424/424 |
| 4,855,141 | 8/1989 | Eckenhoff et al. | 424/473 |

Primary Examiner—C. Fred Rosenbaum
Assistant Examiner—Sharon Finkel
Attorney, Agent, or Firm—Paul L. Sabatine; Edward L. Mandell; Steven F. Stone

[57] ABSTRACT

A delivery system is disclosed for delivering a beneficial agent to an animal. The delivery system comprises a wall that surrounds a lumen, said wall comprising a composition that limits the passage of fluid into the system and a composition that permits the passage of fluid into the system. The lumen comprises a beneficial agent and an expandable member. The delivery system comprises an exit means for delivering the beneficial agent.

5 Claims, 4 Drawing Sheets

FIG.10
FIG.11
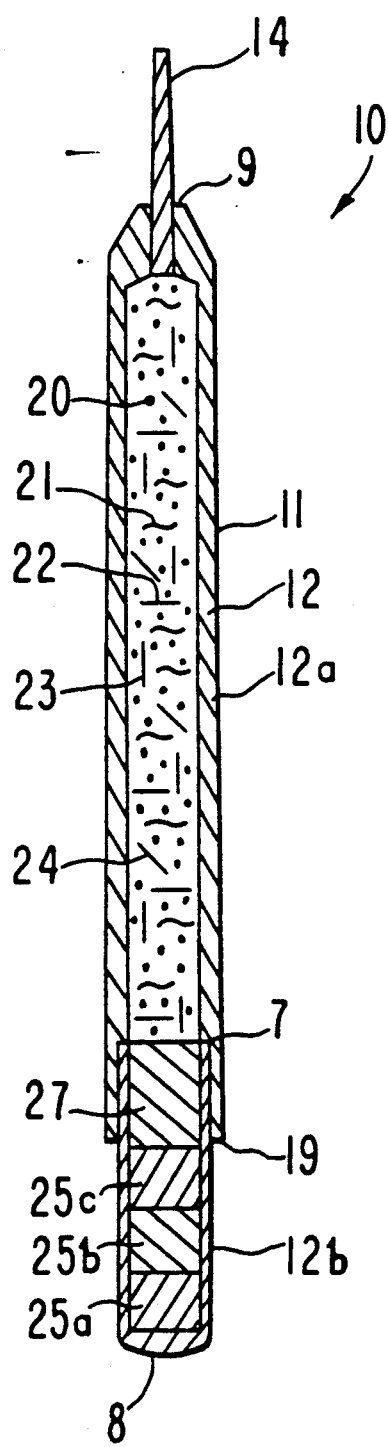
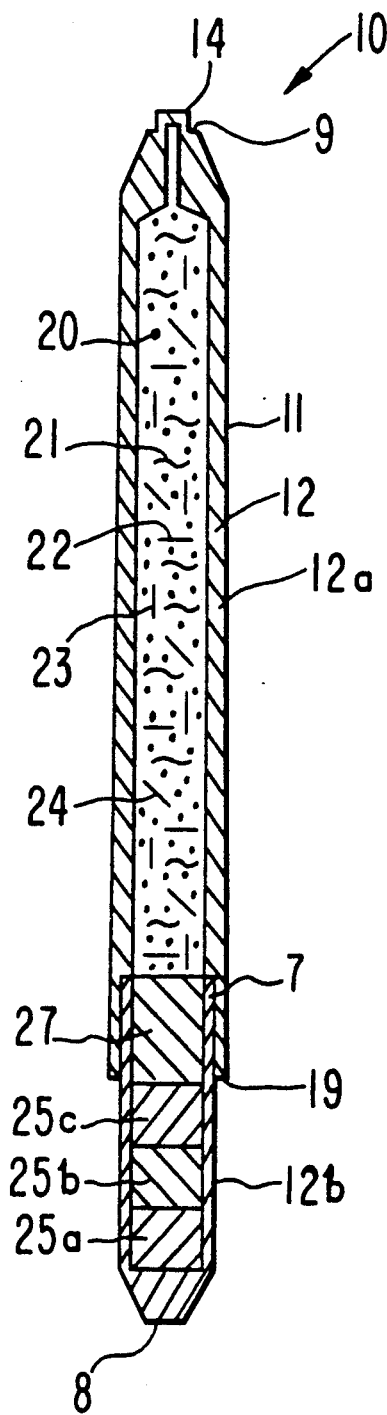

DELIVERY SYSTEM COMPRISING TWO SECTIONS FOR DELIVERING SOMATOTROPIN

CROSS-REFERENCE TO RELATED APPLICATIONS

This application is a division of U.S. Ser. No. 07/283,359 filed on Dec. 13, 1988, which application is incorporated herein by reference, and benefit is claimed of its filing date. These applications are assigned to the ALZA Corporation of Palo Alto, Calif.

FIELD OF THE INVENTION

This invention pertains to both a novel and to an unobvious delivery system. More particularly, the invention relates to a delivery system comprising (1) housing means, (2) a compartment, and (3) exit means. The housing means comprises (a) a section that substantially restricts the ingress of fluid into the delivery system, and (b) a section that permits the ingress of fluid into the delivery system. The compartment comprises (c) a bioavailable and biocompatible beneficial agent formulation and (d) means for delivering the agent formulation from the delivery system. The exit means comprises (e) at least one passageway in the housing means for connecting the exterior with the interior of the delivery system for delivering the agent formulation from the delivery system.

BACKGROUND OF THE INVENTION

Delivery systems for administering a beneficial agent to a biological, fluid environment of use are known to the prior art. For example, U.S. Pat. No. 3,845,770 issued to Theeuwes and Higuchi, and in U.S. Pat. No. 3,916,899 issued to the same patentees, a device is disclosed comprising a wall that surrounds a compartment containing a beneficial agent. The wall is permeable to the passage of fluid and comprises a passageway that is preformed or formed during use through the wall for delivering the beneficial agent from the device. The devices of these patents release the beneficial agent by fluid being imbibed through the wall into the compartment at a rate determined by the permeability of the wall and the osmotic pressure gradient across the wall. The fluid imbibed into the device mixes with the beneficial agent to form an aqueous solution comprising the beneficial agent that is dispensed through the passageway from the device. The devices of these patents are extraordinarily effective for delivering a beneficial agent that is stable and soluble in aqueous and biological fluids and exhibits an osmotic pressure gradient across the wall against the fluid. The devices are effective also for delivering a beneficial agent that is mixed with an osmotically effective solute soluble in fluid that exhibits an osmotic pressure gradient across the wall against an aqueous fluid.

A further advancement in the delivery art for dispensing a stable formulation is disclosed in U.S. Pat. No. 3,995,632 issued to Nakano, Higuchi and Hussain. The dispenser disclosed in this patent dispenses a stable composition that absorbs heat and forms a dispensable melt. The melt is dispensed by a solution of magnesium sulfate increasing in volume and occupying the space originally occupied by the melt.

A quantum improvement in osmotic devices was presented to the pharmaceutical dispensing art by inventor Theeuwes in U.S. Pat. Nos. 4,111,202; 4,111,203; and 4,203,439. In these patents the delivery kinetics of the devices were enhanced for delivering a beneficial agent with different degrees of solubility in an aqueous-type fluid. The kinetics were improved by manufacturing the devices with a beneficial agent compartment separated by a film from an osmotic compartment. The devices deliver the beneficial agent by fluid being imbibed through the wall into the osmotic compartment to fill the compartment with fluid that acts as a driving force and causes the film to move. The film moves against the beneficial agent compartment and the driving force pushes the beneficial agent through a passageway from the device.

A pioneer advancement in osmotic delivery devices was made by Cortese and Theeuwes in U.S. Pat. No. 4,327,725 and by Wong, Barclay, Deters and Theeuwes in U.S. Pat. No. 4,612,008. The devices disclosed in these patents comprise a semipermeable wall that surrounds a compartment. The compartment contains a beneficial agent formulation and a hydrogel. These devices operate by imbibing fluid into the compartment, wherein it contacts the biological agent formulation and forms a dispensable aqueous formulation, and wherein it contacts the hydrogel causing it to expand and push the dispensable aqueous formulation from the device.

The delivery devices described in the above patents operate successfully for their intended use and they can deliver many beneficial agents for their intended effects. Now, it has been observed their use can be limited because they lack the necessary elements to deliver beneficial agents that are sensitive to fluids, and to fluids containing biological gases. Their use may be limited because beneficial agents that are sensitive to such aqueous-biological fluids or to other fluids external to the delivery device may be adversely affected by fluids that enter the device and contact the beneficial agents during operation of the device. Examples of such fluid sensitive agents include proteins and peptides, and hormones. Moreover, the prior art devices lack the necessary means for their use as implant devices for dispensing such sensitive agents to a biological fluid-rich environment of use.

It will be appreciated by those versed in the dispensing arts that if a delivery system is provided for administering at a controlled rate and for protecting a beneficial agent that is sensitive to aqueous and biological fluids, and which delivery system possesses the kinetic ability to deliver the protected beneficial agent in effective amounts over time, such a delivery system would have a positive value and represent an advancement in the dispensing arts. Likewise, it will be self-evident to those versed in the implant art that a pressing need exists for an implant that is essentially-free of the tribulation associated with the prior art, and, that if such an implantable delivery system is provided, it would have a practical application in the fields of human and veterinary medicine and in the breeding and management of farm animals.

OBJECTS OF THE INVENTION

Accordingly, it is an immediate object of this invention to provide a delivery system for delivering a beneficial agent that overcomes the limitations associated with the prior art.

Another object of the invention is to provide a delivery system for delivering in vivo a beneficial agent such as a drug that is difficult to deliver and now can be delivered by the delivery system in therapeutically effective amounts to both humans and livestock.

Another object of the invention is to provide a delivery system comprising means for protecting a beneficial agent from aqueous and biological fluids.

Another object of the invention is to provide a delivery device comprising means for protecting a fluid sensitive biological agent in the device from fluid, and means for administering the beneficial agent to an environment of use, wherein the environment of use may be a fluid, aqueous-biological environment.

Another object of the invention is to provide a delivery system comprising means for storing and for protecting a bioactive beneficial agent formulated in a biocompatible composition during its residency in the delivery system.

Another object of the invention is to provide an implant for livestock that can remain in the livestock until slaughter.

Another object of the invention is to provide a delivery system comprising means for high loading of a beneficial agent essentially-free from its inactivation while in the delivery system, and comprising means for delivering the beneficial agent at a controlled rate and continuously over time to a beneficial agent recipient.

Another object of the invention is to provide a delivery system manufactured as an osmotic therapeutic device comprising a beneficial agent, and which delivery system can administer a complete pharmaceutical dosage regimen at a controlled rate continuously for a particular time period, the use of which delivery system requires intervention only for initiation and the possible termination of the regimen.

Another object of the invention is to provide a delivery system for delivering a drug to an animal, including cattle and hogs, which term, "hogs," includes pigs and porcines, by using a delivery system manufactured as an osmotic device that possesses the ability to deliver the beneficial drug over a broad range of dosage delivery rates according to the predetermined time-release pattern to the biological recipient over time.

Another object of the invention is to provide an osmotic device comprising a compartment containing a drug shielded from a fluid environment of use, and an expandable driving member that operates to diminish the volume occupied by the drug, thereby displacing and thus delivering the drug from the device at a controlled rate over time.

Another object of the invention is to provide a delivery system for delivering a dosage unit amount of a drug to a warm-blooded animal, such as a ruminant or a swine, and which delivery system can be shaped, sized and adapted as an implant for implanting it in the muscle tissue of an animal, the subcutaneous space, the vaginal cavity, or in the peritoneal cavity.

Another object of the invention is to provide an implantable, pharmaceutical delivery system for delivering a beneficial agent to a human or to a veterinary host, with the implant releasing the beneficial agent at a rate controlled by the implant, and when the release of beneficial agent is terminated abruptly, the implantable system leaves a minimal agent residue in the implant and in the host.

Another object of the invention is to provide an implantable delivery system that is implantable by using simple injection techniques and does not require extensive surgery for its placement in a biological tissue.

Another object of the invention is to provide an implant that can be placed under the skin of an animal for releasing an effective amount of a beneficial agent for causing the animal to gain weight at a greater than normal rate, and which implant remains intact and is easily and completely removed for allowing a withdrawal period prior to slaughter.

Another object of the invention is to provide a drug delivery device that is implantable, is compact in size and shape to allow easy placement within the lumen of trocars and similar implanting or injecting instruments that are limited in dimensions and, consequently, are essentially-free of undue trauma and discomfort to a receiving animal.

Another object of the invention is to provide a delivery device shaped at its ends in a conical or spherical shape for reducing the force necessary to push the device into an implantation receiving site, thereby reducing the incidence of tissue damage and the incidence of damage to the delivery device, thereby enhancing the process of implantations.

Another object of the invention is to provide a delivery device comprising ends of a conical or spherical shape for producing a device better designed to withstand elevated interior pressures occurring within the device during hydrodynamic pumping, which shape is of value when the device is delivering high viscosity compositions that create higher pressures during pumping at given flow rates and exit sized passageways.

Another object of the invention is to provide a delivery system that can be placed under the skin of an animal for releasing an effective amount of a beneficial agent for causing increased productivity, which increases in productivity is a result of any combination of the following, higher feed conversion efficiency as exemplified by a greater ration of animal weight gain to amount of feed intake, improved carcass quality as exemplified by a higher ratio of muscle tissue to fat tissue, and a higher than normal rate of animal weight gain.

Another objective of the invention is to provide a delivery device that completely envelops the beneficial, fluid sensitive agent within the protective polymer housing shaped conically or otherwise tapered about a closed exit passageway that can be opened immediately prior to implantation either manually or automatically by snapping-off, or cutting-off the thin tapered closed end, thereby maximizing the period of protection offered by the sealed device and minimizing the opportunity for external environmental contamination of the beneficial agent housed within the device.

Other objects, features and advantages of the invention will be more apparent to those versed in the dispensing art from the following detailed specification taken in conjunction with the accompanying claims.

BRIEF DESCRIPTION OF THE DRAWINGS

In the drawing figures, which are not drawn to scale, but are set forth to illustrate various embodiments of the invention, the drawing figures are as follows:

FIG. 10 is an opened view of a delivery system similar to the delivery system of FIG. 9 with the delivery system of FIG. 10 illustrating a different array of components contained in the delivery system; and, FIG. 11 is an opened view of a delivery system provided by the invention wherein the system embraces another means that closes and is used for forming an exit port in the delivery system.

DETAILED DESCRIPTION OF THE DRAWING FIGURES

Figure 1:
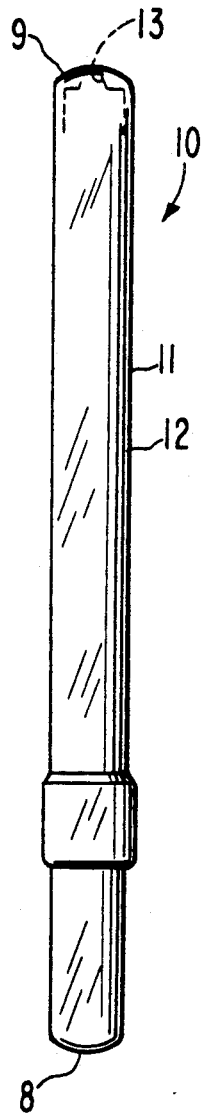
FIG. 1 is a view of a delivery system provided by the invention wherein the delivery system comprises exit means formed during manufacture of the delivery system for delivering a beneficial agent to an environment of use comprising a biological fluid.

Turning now to the drawing figures in detail, which drawing figures are examples of various delivery systems provided by the invention, and which examples are not to be construed as limiting, one example of a delivery system is seen in FIG. 1 as identified by the number 10. In FIG. 1, delivery system 10 comprising a housing 11 formed of a wall 12, which wall surrounds and defines an internal compartment, not seen in FIG. 1. Delivery system 10 comprises at least one exit passageway 13, indicated by a break in wall 12, for delivering a beneficial agent formulation from delivery system 10. In FIG. 1, delivery system 10 comprises a dome-shaped rear end 8 and a similar dome-shaped lead end 9 for aiding in placing delivery system 10 in an animal host. In an embodiment not seen, delivery system 10 can be manufactured with a pair of flat ends 8 and 9. The expression, "lead end," as used herein generally denotes the end from which beneficial agent is released from the system.

Figure 2:
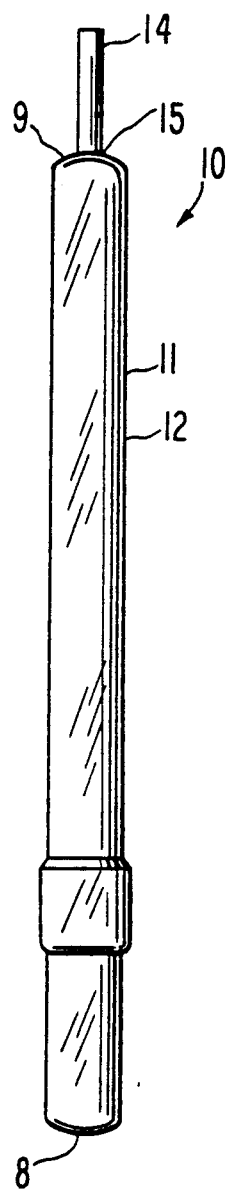
FIG. 2 is a view of a delivery system provided by the invention, which delivery system is similar to the delivery system of FIG. 1, with the delivery system of FIG. 2 comprising the added embodiment of an exit closed by a break-off tip for preventing a premature delivery of a beneficial agent and for preventing contamination of a beneficial agent housed within the delivery system prior to a force being applied to the break-off tip for forming an exit opening in the delivery system.

FIG. 2 depicts another delivery system 10 provided by the invention. In FIG. 2 delivery system 10 comprises housing member 11, which housing member 11 comprises wall 12 that surrounds and forms an internal compartment, not seen in FIG. 2. Delivery system 10 comprises lead end 9 and rear end 8. In FIG. 2, delivery system 10 comprises break-off or severable tab 14 at lead end 9. Break-off or severable tab 14 covers an exit passageway, not seen in FIG. 2. Break-off or severable tab 14 serves several purposes, it seals delivery system 10 for preventing a premature delivery of a beneficial agent from delivery system 10, it helps maintain the sterile environment inside delivery system 10, and it protects the ingredients inside the delivery system from oxidation by air. Break-off tab 14 comprises an optional scored line 15 to enhance its separation from the delivery system. Break-off or severable tab 14 is easily snapped-off at the time of use by manual pressure, by tapping, by twisting, by filing, by cutting, or the like, at the time of use to provide an exit passageway. The break-off tab 14 can be formed during manufacture, it can be jointed to the body member by heat fusion, adhesive joining, or the like.

Figure 3:
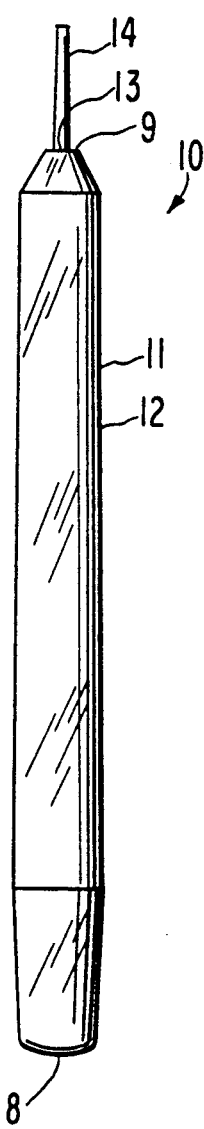
FIG. 3 is a view of a delivery system of the invention, wherein the delivery system comprises another housing arrangement that provides also means for protecting a beneficial agent sensitive to fluid from the fluid.

FIG. 3 depicts another delivery system 10 provided by the invention. In FIG. 3, delivery system 10 comprises body member 11, wall 12, lead end 9, rear end 8, tab 14 closing an exit passageway 13. In FIG. 3, delivery system 10 comprises a substantially uniform housing 11 throughout its dimensions. This structure, when delivery system 10 is designed and shaped with substantially uniform longitudinal and circular dimensions as an implant, provides a means for enhancing its implantable properties into a biological environment comprising muscle tissue, subcutaneous space or other sensitive implant locations.

Figure 4:
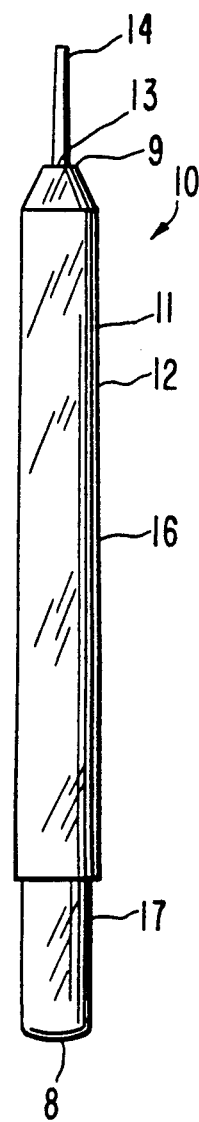
FIG. 4 is a view of another delivery system of the invention, wherein the delivery system comprises a housing embracing a lead end with means for opening the delivery system that is structurally different than the rear end.

FIG. 4 illustrates a delivery system 10 comprising housing member 11, wall 12, exit passageway 13, break-off or severable tab 14, lead end 9 and rear end 8. In this application the expression, "lead end," generally denotes the end the beneficial agent exits the delivery system. In use, either end may be implanted first. In FIG. 4, delivery system 10 housing 11 comprises a first section 16 and a second section 17. The first section 16 and the second section 17 provide (1) an easy method for manufacturing delivery system 10, (2) a means for selectively manufacturing or managing components inside first section 16 differently from components inside second section 17, which can, for example, permit sterilization of section 16 and components therein by, for example, gaseous sterilization without irradiating the beneficial agent, which section 17 can be radiated with sterilizing doses of radiation, (3) a means for replacing one of sections 16 or 17 during use, and (4) as a means for enhancing the implant properties of delivery system 10.

Figure 5:
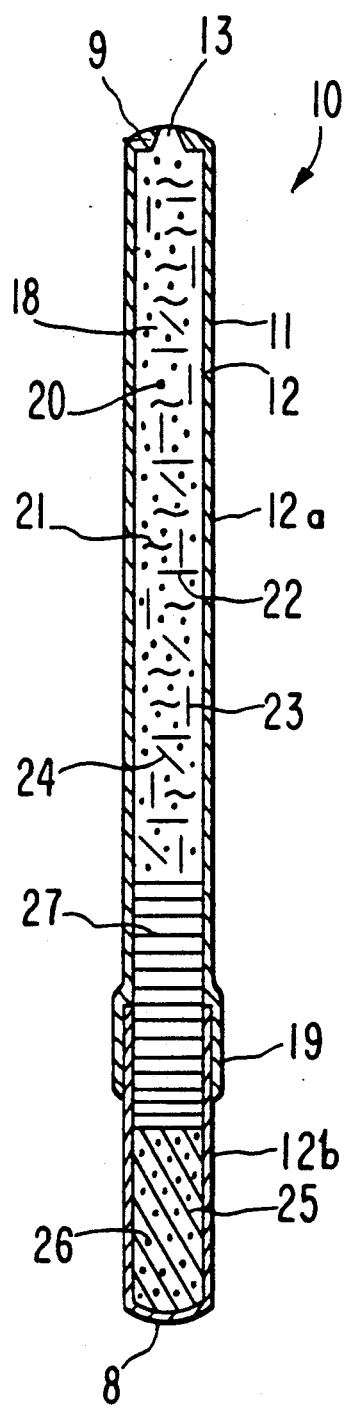
FIG. 5 is an opened view of the delivery system of FIG. 1, illustrating one structural embodiment of the delivery system comprising a first walled section and a second walled section, with the delivery system additionally comprising a preformed manufactured exit passageway and a dome shaped lead and rear end.

FIG. 5 depicts an opened view of delivery system 10 of FIG. 1. Delivery system 10 of FIG. 5 comprises a lead end 9, a trailing end 8 and a passageway 13 that connects the exterior with the interior of delivery system 10. Delivery system 10 comprises also housing member 11. Housing member 11 comprises wall 12, which wall 12 comprises a first wall section 12a and a second wall section 12b. Wall 12, comprising first wall section 12a and second wall section 12b surrounds and defines an internal compartment 18. Wall section 12a is the lead end 9, it forms passageway 13 and it surrounds the internal compartment area 18 that contains a beneficial agent formulation. Wall section 12a at its end distant from lead end 9 defines and forms receiving means 19. Receiving means 19 is enlarged slightly for receiving second wall section 12b. Wall section 12b surrounds the internal compartment area 18 that contains a means for expanding and for occupying space in compartment 18 for delivery of a beneficial agent formulation from delivery system 10. The two wall sections, sections 12a and 12b at receiving end 19, are close in size and they form a tight friction fit therebetween. There is clearance or tolerance in size to allow wall section 12b a sliding movement into the receiving means 19 of wall section 12a. Wall section 12a and wall section 12b can be telescoped completely into a closed, and continuous walled position. Optionally, they can be held together by heat fusion, by an adhesive, or the like.

Wall section 12a comprises a composition that is substantially impermeable to the exchange of fluid, beneficial agent and other ingredients contained in delivery system 10. Wall section 12a, in a presently preferred manufacture, is substantially impermeable to the ingress of an external fluid to serve as a means for substantially protecting a beneficial agent that is sensitive to fluid from an exterior fluid present in the environment of use. Wall section 12a substantially restricts and prevents fluid from passing through wall 12a and entering into compartment 18 in the region containing a beneficial agent formulation. Wall section 12b comprises in at least a part a semipermeable wall composition that is permeable to the passage of fluid for making available fluid to an expandable driving means inside compartment 18. Wall section 12b is permeable to the passage of fluid and it is substantially impermeable to the passage of other ingredients contained in delivery system 10. Wall sections 12a and 12b optionally comprise a plasticizer that imparts flexibility and workability to the wall. Wall 12, comprising sections 12a and 12b, is non-toxic and, in a preferred embodiment, it maintains its physical and chemical integrity, that is, wall 12 does not erode during the dispensing period.

Compartment 18 comprises a beneficial agent formulation, which beneficial agent formulation comprises a beneficial agent 20 identified by dots, and a pharmaceutically acceptable carrier 21 identified by wavy lines. The pharmaceutically acceptable carrier in one presently preferred embodiment comprises more than one ingredient, such as a buffer 22 identified by horizontal dashes; a pharmaceutically acceptable vehicle 23 identified by vertical lines; a pharmaceutically acceptable surfactant 24 identified by slanted lines, and other formulation ingredients. Compartment 18 further comprises an expandable driving member 25 identified by slanted lines. Expandable driving member 25 optionally comprises an osmagent 26, identified by dots, homogeneously or heterogeneously blended with expandable driving member 25. Compartment 18 optionally comprises a layer 27, represented by horizontal lines, which layer 27 is positioned between the beneficial agent formulation and the expandable driving member 25. Layer 27, in a presently preferred embodiment, comprises a composition that is substantially impermeable to the passage of fluid and it serves to restrict the passage of fluid present in the expandable driving member into the beneficial agent formulation; and it operates to essentially maintain the integrity of the beneficial agent layer and the driving layer. Layer 27 acts also to insure that the expanding driving force generated by the expandable driving member is applied directly against the beneficial agent formulation. In operation, as the expandable member 25 absorbs and imbibes fluid, it expands and pushes against layer 27 causing it to slide inside compartment 18. Layer 27 moves towards passageway 13, pushing the beneficial agent formulation through passageway 13 for maximizing the delivery of the beneficial agent to a biological environment of use, such as livestock.

Figure 6:
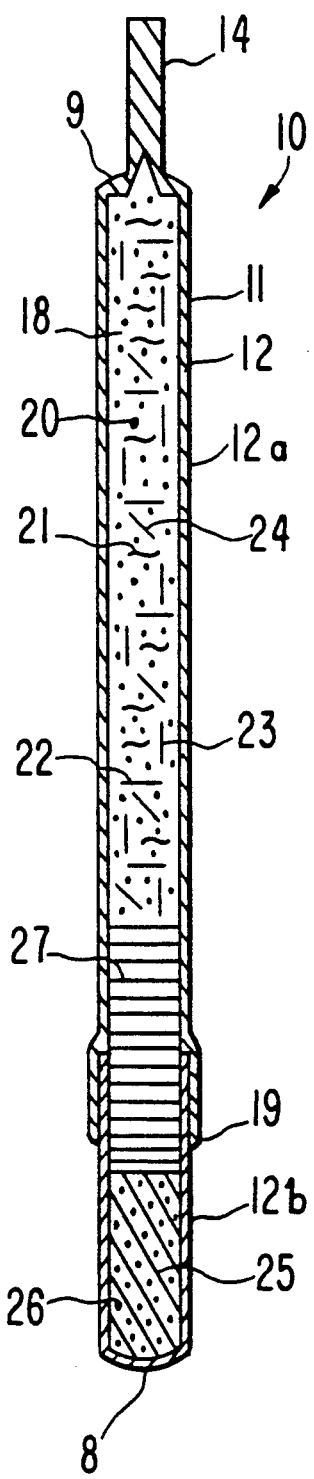
FIG. 6 is an opened view of the delivery system of FIG. 2 illustrating the structure of the delivery system comprising a first and a second walled section, and a break-off tip that is easily broken-off at the time of use for providing an exit passageway.

FIG. 6 is an opened view of FIG. 2 for depicting the structure of delivery system 10. Delivery system 10 of FIG. 6 comprises housing member 11, lead end 9, rear end 8, wall 12, first wall section 12a, second wall section 12b, receiving end 19 of first wall section 12a, internal space 18, beneficial agent 20, pharmaceutically acceptable carrier 21, nontoxic buffer 22, nontoxic vehicle 23, nontoxic surfactant 24, expandable driving member 25, osmotically effective solute 26 and force transmitting layer 27. In FIG. 6, delivery system 10 comprises also break-off tab 14. Break-off or removable tab 14 is broken-off or severed easily from body member 11 by holding tab 14 between the index finger and the thumb of one hand, and by holding body member 11 between the index finger and the thumb of the other hand and snapping the assembly to form an exit passageway. Tab 14 can also be severed by cutting, filing, and the like.

Figure 7:
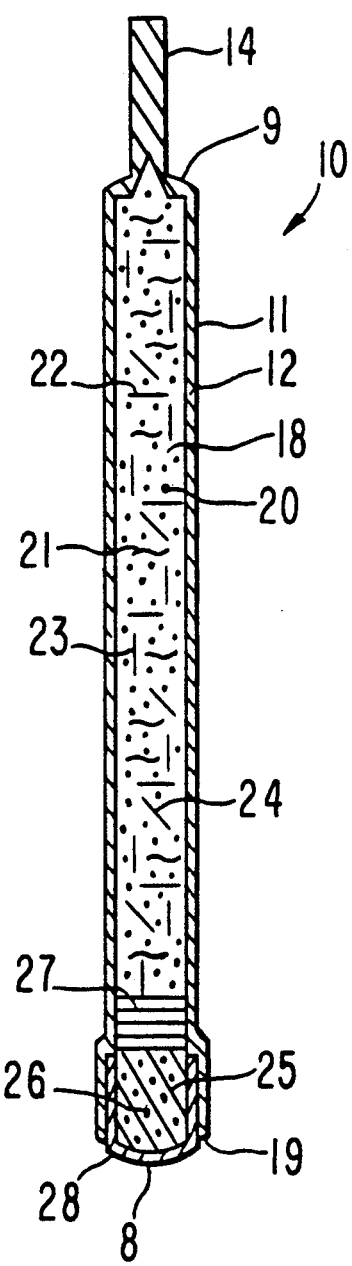
FIG. 7 is an opened view of a delivery system provided by the invention depicting the delivery system comprising a housing member provided with means for releasably holding an insert member comprising an expandable composition for pushing a beneficial agent formulation from the delivery system.

FIG. 7 is an opened view of another embodiment of delivery system 10 provided by the invention. In FIG. 7, delivery system 10 comprises housing member 11, wall 12, lead end 9, rear end 8, break-off tab 14, internal compartment 18 that contains beneficial agent 20, pharmaceutically acceptable carrier 21, nontoxic buffer 22, nontoxic agent vehicle 23 which vehicle 23 also functions as a viscosity enhancer, and a nontoxic surfactant 24. In FIG. 7, wall 12 is continuous and it extends the length of delivery system 10. Wall 12, at its end 8 distant from lead end 9, comprises a receiving end 19. Receiving end 19 is designed and adapted for receiving insert 28. Insert 28 is cup-like in shape, or tube-like with a single closed end, and it is made of a composition such a polymeric composition that is permeable to the passage of an external fluid. Insert 28 comprises an expandable volume consuming member 25 comprising an optional osmotically effective solute 26, and a layer or partition 27 that separates expandable member 25 from the other ingredients present in compartment 18. Insert 28 in end 19, in a presently preferred embodiment, is replaceable and one or more than one insert 28 can be used during the operation of delivery system 10.

Figure 8:
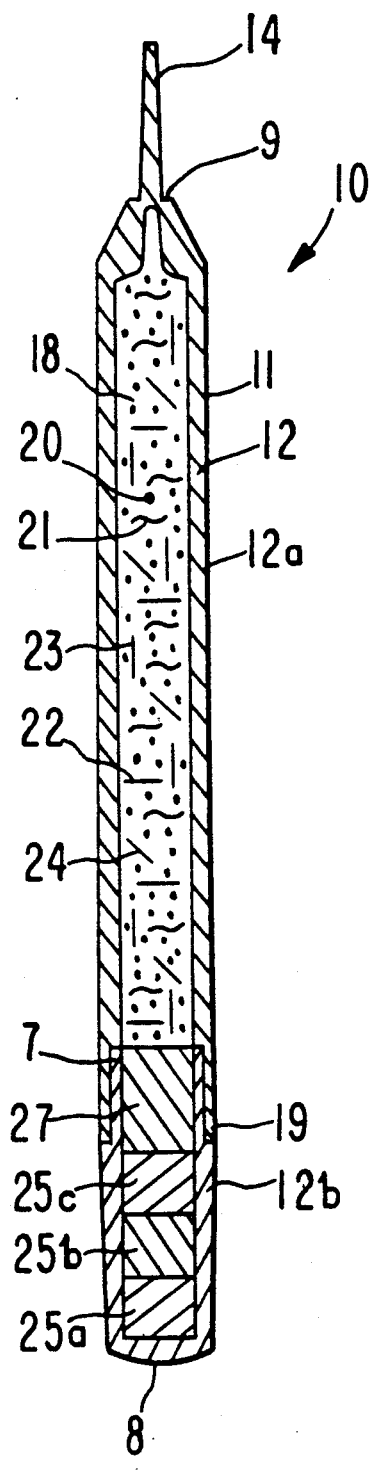
FIG. 8 is an opened view of the delivery system of FIG. 3, wherein the delivery system comprises a first walled member and an engaging second walled member, and the opened viewed system also depicts the components contained in each walled member.

FIG. 8 is an opened view of the delivery system 10 illustrated in accompanying FIG. 3. In FIG. 8, delivery system 10 comprises housing member 11 formed by wall 12. Wall 12 comprises (1) a first section 12a that surrounds an internal compartment area containing a beneficial agent, and (2) a second section 12b that surrounds an internal compartment area comprising at least one means for occupying space in the compartment. First wall section 12a is provided with receiving means 19. Wall 12a at receiving means 19 is thinner and it exhibits a smaller internal dimensions for receiving second section 12b at its opened end 7. Wall section 12b is thinner at its opened end 7 and it exhibits a smaller external dimensions for sliding into receiving end 19 in mated relation for providing an essentially continuous wall 12. The two sections can be joined together by various techniques such as solvent weld, adhesive bond, thermal weld, ultrasonic weld, spin weld, induction weld, or by similar welding or bonding operations. First wall section 12a and second wall section 12b in the delivery system 10 seen in FIG. 8 are substantially uniform in cross-sectional dimensions thereby providing delivery system 10 with substantially uniform dimensions along its central axis. Delivery system 10 in FIG. 8 also comprises lead end 9, rear end 8, break-off tab 14, internal compartment 18, beneficial agent 20, pharmaceutically acceptable carrier 21, pharmaceutically acceptable vehicle 23, and a pharmaceutically acceptable solvent 24. In a presently preferred embodiment delivery system 10 comprises a multiplicity of expandable driving member 25a, 25b and 25c. Expandable driving members 25a, 25b and 25c comprise like or unlike compositions. For example, members 25a, 25b and 25c can be made as tablets comprising like osmopolymers or like osmagents, or they can comprise unlike osmopolymers or unlike osmagents. The osmopolymers and the osmagents can be made as tablets and inserted through open end 7 successively into second wall member 12b. Also, member 25a, 25b and 25c can be different. For example, member 25a comprises an osmopolymer, member 25b comprises an osmagent, and member 25c comprises an osmopolymer, or member 25a comprises an osmagent, member 25a comprises an osmopolymer, and member 25c comprises an osmagent, and the like. Delivery system 10 in a presently preferred manufacture comprises layer 27 that separates the beneficial agent formulation from the expandable driving members.

Figure 9:
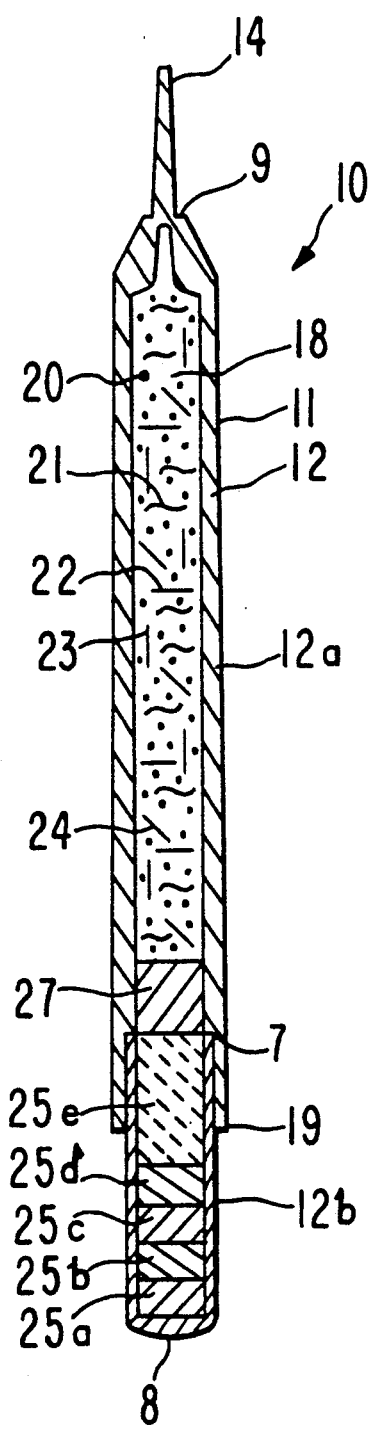
FIG. 9 is an opened view of the delivery system of FIG. 4 depicting a delivery system comprising a beneficial agent section and a driving force section joined as releasable engaging structural member sections to provide an integral delivery system.

FIG. 9 is an opened view of the delivery system 10 illustrated in FIG. 4. In FIG. 9, delivery system 10 comprises housing member 11, wall 12 comprising first section 12a, second section 12b, lead end 9, rear end 8, break-off tab 14, receiving means 19, opening 7 in wall member 12b, beneficial agent 20, pharmaceutically acceptable carrier 21, pharmaceutically acceptable buffer 22, pharmaceutically acceptable viscosity enhancing vehicle 23, and a pharmaceutically acceptable surfactant 24. In FIG. 9, the first section 12a functions as a first body portion 12a of delivery system 10, and it is designed for slipping over, or for receiving second section 12b that serves as a second body portion 12b. The second body portion is telescopically capped by the engaging first body portion 12a. In FIG. 9, delivery system 10 comprises a partition 27 positioned near the filling end of first section 12a, and at the filling entrance of second section 12b comprises a plurality of driving members 25a, 25b, 25c, 25d and 25e. The members are presently formed as depots or layers of the same or different member forming composition selected from the group consisting of an osmopolymer, an osmagent, or a composition comprising an osmopolymer and an osmagent.

FIG. 10 is an opened view of FIG. 4 taken in conjunction with FIG. 6 for illustrating the structure of delivery system 10. In FIG. 10, delivery system 10 comprises housing member 11, wall 12 comprising first section 12a, second section 12b, lead end 9, rear end 8, break-off tab 14, receiving end 19, opening 7, beneficial agent 20, pharmaceutically acceptable carrier 21, pharmaceutically acceptable buffer 22, pharmaceutically acceptable viscosity modulating vehicle 23, pharmaceutically acceptable surfactant 24, non-toxic partition 27, and driving members 25a, 25b and 25c selected from the group consisting of an osmopolymer, an osmagent, and an osmopolymer containing an osmagent. In FIG. 10, one example of delivery system 10 is manufactured as an implant comprising a body length of about 50.12 mm, a diameter of about 4.97 mm, the beneficial agent formulation occupying a length of 33.27 mm, a partition occupying a space of 5.08 mm, and an initial total space of 7.62 mm occupied by the expandable members. The optional break-off tab is about 6.07 mm in length and when broken off it forms an exit passageway of 0.64 mm. The implant can be implanted into receiving tissue using an implanter. Generally, an implanter comprises a tubular member with a central longitudinal axial bore, a pointed, elongated, annular concavely beveled implanting end and an implant charging end. The implanting end and the charging end communicate through a bore. A plunger adapted to be removably inserted in the bore is designed for slidable movement therein for applying the necessary force for implanting the implant. Also, the implant can be surgically implanted in the muscle or other tissue of livestock.

In drawing FIG. 11, a dosage form 10 is seen in opened section, which dosage delivery form 10 is similar in structure and in operation to delivery form 10 illustrated in drawing FIG. 10. In drawing FIG. 11, dosage form 10 comprises a shortened tab 14. The shortened tab 14 is sheared, cut-off, severed, pryed-off, bent or broken-off in an implant injection device. The shortened tab 14 also can be snapped-off by pushing tab 14 against a sterile surface, prior to implanting it in livestock. In FIG. 11, system 10 also comprises a tapered end 8.

The delivery systems 10 of FIGS. 1 through 11 can be manufactured for delivering numerous beneficial agents, including drugs at a controlled rate, to a presently preferred biological environment of use such as warm-blooded animals including humans, ruminants, hog, swine, porcine and the like. The delivery system provides for high loading of a beneficial agent and for its delivery in beneficially effective amounts over time. It is to be understood the delivery systems are not to be construed as limiting, as the delivery systems can take a wide variety of shapes, sizes and forms adapted for delivering beneficial agents to environments of use. For example, the delivery systems manufactured as delivery devices can be used for dispensing a beneficial agent in the anal-rectal passageway, in the cervical canal, as an artificial gland, in the vagina, as a subcutaneous implant, and the like. The delivery system can be used in hospitals, nursing homes, outpatient clinics, veterinary clinics, sickrooms, farms, zoos and other environments of use.

DETAILED DESCRIPTIONS OF THE INVENTION

In accordance with the practice of this invention, it has now been found that delivery system 10 can be manufactured with a first wall section 12a that surrounds the compartment's internal space initially occupied by the beneficial agent formulation. First wall section 12a comprises a composition that does not adversely effect the beneficial agent, the osmopolymer, the osmagent, other ingredients in delivery system 10, the host, or the like. First wall section 12a comprises a composition that is a means that substantially limits or prevents the passage of an external fluid into delivery system 10. The phrase, "substantially limits or prevents," as used herein, indicates the volume of external fluid passing through first section wall 12a is substantially negligible, that is, about zero up to about 1 $\mu$ or up to about 1 ml per day. Typical compositions for forming first section 12a are vinylidene chloride copolymers and terpolymers such as vinylidene chloride-vinyl chloride copolymer, vinylidene chloride-acrylonitrile copolymer, vinylidene chloride-styrene copolymer, and vinylidene chloride-vinyl chloride-acrylonitrile terpolymer; acrylonitrile polymers such as acrylonitrile-methyl vinyl ether copolmer, acrylonitrile-styrene copolymer, acrylonitrile-butadiene-styrene terpolymer, and the like; halogenated polymers such as chlorinated polyether, polytetrafluroethylene, polychlorotrifluoroethylene, copolymer tetrafluroethylene and hexafluropropylene, polyvinylfluoride, polyvinyl-chlorobuteral, plasticized polyvinylidene chloride, and the like; nylon; polyamide-imide; polyarylether; polysulfone; polycarbonate; high density polyethylene; polyvinylchloride-acrylic copolymer; polycarbonate-acrylonitrile-butadiene-styrene; glass; bakelite; melamine; polystyrene; stainless steel, and the like. The water vapor transmission rate through compositions useful for forming first wall 12a are reported in *J. Pharm. Sci.*, Vol. 59, pp 1634–37, (1970); in *Ind. Eng., Chem.*, Vol. 45, pp 2296–2306, (1953); *Materials Engineering*, Vol. 5, pp 38–45, (1972); in *Ann. Book of ASTM Stds.*, Vol. 08.02, pp 208–11 and pp 584–87, (1984); and in *Ind. and Engin. Chem.*, Vol. 49, pp 1933–36, (1957). The polymers are known in the *Handbook of Common Polymers*, by Scott and Roff, CRC Press, Cleveland Rubber Co., Cleveland, Ohio.

The second wall section 12b comprises a composition comprising means that aids in controlling fluid flux into the compartment area occupied by the expandable driving member. The composition is permeable to the passage of external fluids such as water and biological fluids, and it is substantially impermeable to the passage of beneficial agents, osmopolymers, osmagents, and the like. Typical compositions comprise semipermeable materials for forming wall 12b are, in one presently preferred embodiment, a member selected from the group consisting of a cellulose ester, a cellulose ether and a cellulose ester-ether. These cellulosic polymers have a degree of substitution, D.S., on the anhydroglucose unit, from greater than 0 up to 3 inclusive. By, "degree of substitution," or "D.S.," is meant the average number of hydroxyl groups originally present on the anhydroglucose unit comprising the cellulose polymer that are replaced by a substituting group. Representative materials include, but are not limited to, a member selected from the group consisting of cellulose acylate, cellulose diacylate, cellulose triacylate, cellulose acetate, cellulose diacetate, cellulose triacetate, mono-, di-, and tricellulose alkanylates, mono-, di-, and tricellulose aroylates, and the like. Exemplary cellulosic polymers include cellulose acetate having a D.S. up to 1 and an acetyl content up to 21%; cellulose acetate having a D.S. of 1 to 2 and an acetyl content of 21% to 35%; cellulose acetate having a D.S. of 2 to 3 and an acetyl content of 35% to 44.8%, and the like. More specific cellulosic polymers include cellulose propionate having a D.S. of 1.8 and a propionyl content of 39.2% to 45% and a hydroxyl content of 2.8% to 5.4%; cellulose acetate butyrate having a D.S. of 1.8 and an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose acetate butyrate having a D.S. of 1.8, and acetyl content of 4% average weight percent and a butyryl content of 51%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentate; coesters of cellulose such as cellulose acetate butyrate and cellulose, cellulose acetate propionate, and the like. The amount of semipermeable materials presently preferred in wall 12b is about 20% to 100%.

Representative materials that can be used to regulate further the fluid flux of wall 12b include materials that decrease the fluid flux and materials that increase the fluid flux of wall 12b. Materials optionally added to wall 12b for decreasing the flux comprise a member selected from the group consisting of polyacrylate; polymethacrylate; polysulfone; polyacrylic ester; polyacrylonitrile; polyacrylamide; polystyrene; polycaprolactam; polyhexamethylene adipamide; polyhexamethylene sebacamide; polyepoxide; polyformaldehyde, and the like. Materials that increase the permeability of wall section 12b to the passage of an exterior fluid include polyvinyl alcohol; poly(1,4-anhydro-beta-D-mannuronic acid); polyester derived from the condensation of a polyhydric alcohol and a polyfunctional acid wherein the functionality refers to reactive groups such as hydroxyl, carboxyl, and the like; polysaccharides; hydroxy alkylcellulose having a molecular weight of 9,000 to 35,000; polyalkylene glycol, and the like. The concentration of means for regulating the flux in wall 12b is about 5% to 50%.

The fluid flux through wall 12 comprising a polymeric composition can be measured by techniques known to the art. One technique that has been found to be eminently well-suited is to cast or hot press a film of the composition to a thickness in the range of 1 to 60 mils. The film is used as a barrier between a fluid source and a container initially free of fluid. Then, by measuring the volume of fluid that passed through a film of known area and thickness, the flux is easily ascertained by standard techniques known to the art as recorded in *J. Pharm. Sci.*, Vol. 52, pp 1145–49, (1963); ibid., Vol. 53, pp 798–802, (1964); ibid., Vol. 54, pp 1459–64, (1965); ibid., Vol. 55, pp 840–43 and pp 1224–39, (1966); *Encycl. Polymer. Sci. Technol.*, Vol. 5 and 9, pp 65–82, and pp 794–807, (1968), and references cited therein; in U.S. Pat. Nos. 3,854,480; 3,845,761 and 3,896,819. Second wall 12b section that exhibit a fluid permeability of $10^{-6}$ to $10^{-1}$ (cc.mil/cm$^2$.hr atm) can be used for the purpose of this invention. The polymers are known to the art in the *Handbook of Common Polymers*, by J. R. Scott and W. J. Roff, (1971), published by CRC Press, Cleveland, Ohio.

First wall section 12a and second wall section 12b optionally comprise a non-toxic plasticizer. Representative plasticizers suitable for forming wall 12a and wall 12b include plasticizers that lower the temperature of the second-order phase of transition of wall 12a and wall 12b, or the elastic modules of wall 12a and wall 12b; also the plasticizers increase the workability of wall 12a and wall 12b and their flexibility. Plasticizers operable for the present purpose include straight chain and branched chain plasticizers, cyclic plasticizers, acrylic plasticizers and heterolcyclic plasticizers. Representative plasticizers include a member selected from the group consistent of phthalate, phosphate, citrate, adipate, tartrate, sebacate, succinate, glycolate, glycerolate, benzoate, myristate, sulfonamide and halogenated plasticizer. Generally wall 12a or wall 12b will comprise from 1% to 45% plasticizers or more, with the total concentration of all ingredients in a wall equal to 100%.

Representative plasticizers include dialkyl phthalate, dicycloalkyl phthalate, diaryl phthalate, dimethyl phthalate, dipropyl phthalate, di(2-ethylhexyl) phthalate, di-isopropyl phthalate, alkyl phosphate, aryl phosphate, tributyl phosphate, trioctyl phosphate, tricresyl phosphate and triphenyl phosphate; alkyl citrate, citrate esters, tributyl citrate, triethyl citrate and acetyl triethyl citrate; alkyl adipates such as dioctyl adipate, diethyl adipate and di(2-methoxyethyl)-adipate; dialkyl tartrates such as diethyl tartrate, and butyl tartrate; alkyl sebacates such as diethyl sebacate, dipropyl sebacate and dinonyl sebacate; alkyl succinates such as diethyl succinate and dimethyl succinate; alkylglycolates, alkyl glycerolates, glycol esters and glycerol esters such as glycerol diacetate, glycerol triacetate, glycerol monolactate diacetate, methyl phythayl ethyl glycolate, and the like.

Suitable plasticizers can be selected for blending with the wall 12a or wall 12b forming materials by selecting plasticizers that have a high degree of solvent power for the materials, are compatible with the materials over both the processing and use temperature range, exhibit permanence as seen by its strong tendency to remain in the plasticized wall, both in storage and in the biological environment of use, imparts flexibility to the material, and are non-toxic to animals, humans, avians, fishes and reptiles. Procedures for selecting a plasticizer having the described characteristics are disclosed in the *Encyclopedia of Polymer Sciences and Technology*, Vol. 10, pp 118–306, (1969), published by John Wiley & Sons, Inc. Also, a detailed description pertaining to the measurement of plasticizer properties including solvent parameters and compatibility, such as the Hildebrand solubility parameter $\delta$, the Flory-Huggins interaction parameter $\mu$, and the Flory-Huggins interaction parameter $\mu$, and the cohesive-energy density, CED, parameters are disclosed in "Plasticization and Plasticizer Processes," *Advances in Chemistry*, Series 48, Chapt. 1, pp 1–26, (1965), published by the American Chemical Society, and in U.S. Pat. No. 4,077,407.

Delivery system 10 in its compartment 18 comprises a beneficial agent 20 that produces a desired and useful result when administered to a warm-blooded animal including humans and farm animals. The beneficial agent 20 is useful in one embodiment for increasing the rate of growth and the efficiency of feed utilization in equine, bovine and swine. The beneficial agent 20 in another embodiment is useful for controlling estrus and ovulation in the course of breeding farm animals for commercial purposes, for effecting contraception and for producing an anabolic response associated with the inhibition of estrus. Beneficial agent 20 in another embodiment is a drug useful for producing a therapeutic effect. The beneficial agent 20 that can be administered by delivery device 10, as provided by the invention, comprises beneficial agents 20 that act at synaptic and neuroeffector sites, beneficial agents acting on the central nervous system, autocoids, anti-inflammatory, analgesic, antipyretic, cardiovascular, and the like.

Representative beneficial agent 20 that can be administered by delivery system 10 include pharmacologically active peptides and proteins, anabolic hormones, growth promoting hormones, hormones related to the endocrine system comprising porcine growth promoting hormone, bovine growth promoting hormone, equine growth promoting hormone, ovine growth promoting hormone, human growth promoting hormone, growth promoting hormones derived by extraction and concentration from pituitary and hypothalmus glands, growth promoting hormones produced by recombinant DNA methods, bovine growth promoting hormone as described in *Nucleic Acid Res.*, Vol. 10, p 7197 (1982), ovine growth promoting hormone as described in *Arch. Biochem. Biophys.*, Vol. 156, p 493 (1973), and porcine growth promoting hormone as described in *DNA*, Vol. 2, pp 37, 45, (1983). The polypeptides also comprise growth hormone, somatropin, somatotropin, somatotropin analogues, modified porcine somatotropin, modified bovine somatotropin, derivatives of both porcine and bovine somatotropin, somatomedin-C, gonadotropic releasing hormone, follicle stimulating hormone, luteinizing hormone, LH-RH, growth hormone releasing factor, gonadotropin releasing factor, insulin, colchicine, chorionic gonadotropin, oxytocin, somatotropin plus an amino acid, vasopressin, adrenocorticotrophic hormone, epidermal growth factor, prolactin, somatostatin, somatotropin plus a protein, cosyntropin, lypressin, polypeptides such as thyrotropin releasing hormone, thyroid stimulating hormone, secretin, pancreozymin, enkephalin, glucagon, endocrine agents secreted internally and distributed in an animal by way of the bloodstream, and the like. The beneficial agents and their dosage unit amounts are known to the prior art in *The Pharmacological Basis of Therapeutics*, by Gilman, Goodman, Rall and Murad, 7th Ed., (1985) published by MacMillan Publishing Co., N.Y.; in *Pharmaceutical Sciences*, Remington, 17th Ed., (1985) published by Mack Publishing Co., Easton, Pa., and in U.S. Pat. No. 4,526,938. Generally, the delivery system 10 comprises from about 5 nanograms to 20 grams of beneficial agent 20.

Pharmaceutical carrier 21, in compartment 18, comprise beneficial agent 20, pharmaceutically acceptable viscosity modulating vehicle 23, a buffer 22, or a buffer solution 22 and a surfactant 24. The pharmaceutically acceptable viscosity modulating means 23 in a presently preferred embodiment comprises a polyol such as a diol, triol, polyhydric alcohol, and the like. More specific polyols comprise 1,5-pentylene glycol; 1,6-hexylene glycol; 1,7-heptylene glycol; 1,9-nonylene glycol; 1,2-dimethyl-1,6-hexylene glycol; 1,2,3-propanetriol; 1,2,5-pentanetriol; 1,3,5-pentanetriol; 1,2,4-butanetriol; dipentaerythriol, and the like. In another embodiment the pharmaceutically acceptable vehicle 23 comprises glycerol mono(lower alkyl) ethers and glycerol di(lower alkyl) ethers such as glycerol 1-methyl ether; glycerol 1-ethyl ether; glycerol 1,2-dimethyl ether; glycerol 1,3-dimethyl ether, and the like. In another embodiment the pharmaceutically acceptable vehicle 23 comprises a mixture such as propylene glycol and glycerol; a mixture comprising propylene glycol, ethanol and glycerol, and the like. The pharmaceutically acceptable vehicle 23 functions as a viscosity modulating means for the components present in a compartment 18, as a vehicle for transporting beneficial agent 18 from compartment 20, it provides protection against the decomposition of a beneficial agent, and it imparts physical chemical stability to components present in compartment 18. The viscosity modulating vehicle may be used to increase the viscosity of the formulation to prevent mixing fluids in the implantation environment from mixing with the beneficial agent carried in formulation within compartment 18. The pharmaceutically acceptable modulating means 23 is present in the compartment 18 is about 0.1% to 90%.

Representative pharmaceutically acceptable buffers 22, in compartment 18, that are blended with the beneficial agent 20 and the pharmaceutically acceptable fluid 23 comprise nontoxic buffer and solution thereof, solutions that resist change of pH thereby giving stability to the components present in compartment 18. In another embodiment the buffer and solutions thereof can be used alone and, in a presently preferred embodiment, the buffer and solution thereof is used in combination with the pharmaceutically and pharmacologically acceptable aqueous miscible fluids. Typical buffer aqueous solutions comprise sodium dihydrogen phosphate (0.025M) and disodium monohydrogen phosphate (0.025M); sodium dihydrogen phosphate (0.025M), disodium monohydrogen phosphate (0.025M) and sodium chloride (0.15M); sodium carbonate (0.025M), sodium monohydrogen carbonate (0.025M) and sodium chloride (0.15M); potassium dihydrogen phosphate (0.025M) and sodium monohydrogen phosphate (0.025M); potassium dihydrogen phosphate (0.0087M) and sodium monohydrogen phosphate (0.0302M); potassium hydrogen tartrate (0.034M) and potassium dihydrogen phosphate (0.025M); acetic acid (0.1M) and sodium acetate (0.1M), and the like. The buffers comprise also citric acid and sodium hydroxide; potassium hydrogen phthatate and sodium hydroxide; potassium hydrogen phosphate and sodium phosphate; tris(hydroxymethyl) aminomethane and hydrochloric acid; sodium tetraborate and hydrochloric acid; glycine and hydrochloric acid; triethanolamine and hydrochloric acid; N-tris (hydroxymethyl)methyl-2-amino sulfonic acid and sodium hydroxide, and the like. The buffer aqueous solution in another embodiment can comprise a sole component such as sodium phosphate monobasic, sodium phosphate dibasic, potassium hydrogen tartrate, potassium dihydrogen citrate, potassium hydrogen phthalate, sodium tetraborate, sodium carbonate, sodium hydrogen carbonate and the like.

Representative pharmaceutically acceptable surfactants 24 for the present purpose comprise anionic, cationic, amphoteric and nonionic surfactants. More specific examples of surfactants comprise sorbitan trioleate, sorbitan tristearate, propylene glycol monostearate; sorbitan sesquiolate; glycerol monostearate; sorbitan monooleate; propylene glycol monolaurate; sorbitan monostearate; diethylene glycol monostearate; glycerol monostearate; diethylmonolaurate; sorbitan monopalmitate; sorbitan monolaurate; polyoxyethylene lauryl ether; polyoxyethylene sorbitan monostearate; polyoxyethylene sorbitan monooleate; polyoxyethylene sorbitan tristearate; polyoxyethylene sorbitan trioleate; polyoxyethylene glycol monooleate; polyoxyethylene glycol monostearate; triethanolamine oleate; polyoxyethylene monyl phenol; polyethylene glycol monolaurate; polyoxyethylene sorbitan monolaurate; polyoxyethylene sorbitan monostearate; polyoxyethylene sorbitan monooleate; polyoxyethylene stearyl ether; polyoxyethylene oleyl ether; polyoxyethylene sorbitan monopalmitate; polyoxyethylene cetyl ether; polyoxyethylene stearate; sodium oleate; potassium oleate; cetyl ethyl morpholinium ethosulfate; sodium lauryl sulfate; sodium caprylate; sodium caprate; sodium laurate; sodium myristate; sodium cholate; sodium desoxycholate; sodium dihydrocholate; tetradecyltrimethyl ammonium bromide; hexadecylpyridinium chloride; Tween 20; Tween 30; Tween 80, and the like. The amount of surfactant used for producing a pharmaceutically acceptable carrier comprising the beneficial agent, the buffer, the pharmaceutically acceptable fluid, is about 0.001% to 7.5%. Generally, the compartment 18 composition comprises from 0.5% to 50% beneficial agent, from 20% to 45% aqueous buffer, from 10% to 75% pharmaceutical viscosity modifying means, and from 0.001% to 7.5% surfactant, with the total of all components 100%; and in a more preferred embodiment the composition comprises 25% to 35% beneficial agent, 25% to 35% aqueous buffer solution, 25% to 50% pharmaceutically acceptable viscosity modifying vehicle, and 0.01% to 1% surfactant, with the total of all components 100%. The pharmaceutically acceptable fluid carrier members and the surfactants are known in *Pharmaceutical Science*, by Remington, 14 Ed., (1970), published by Mack Publishing Co., Easton, Pa., and the buffers are known in *Lange's Handbook of Chemists*, 13th Ed., (1985), published by McGraw-Hill Co., New York, N.Y.

The expandable driving means 25 operable for pushing the beneficial agent composition 20 from delivery system 10, comprises, in a presently preferred embodiment, a swellable hydrophilic polymer. Hydrophilic polymers are known also as osmopolymers. The osmopolymers interact with water and aqueous biological fluids and swell or expand to an equilibrium state. The osmopolymers exhibit the ability to swell in water and to retain a significant portion of the imbibed and absorbed water within the polymer structure. The osmopolymers swell or expand to a very high degree, usually exhibiting a 2 to 50 fold volume increase. The osmopolymers can be noncross-linked or cross-linked. The swellable, hydrophilic polymers are, in one presently preferred embodiment, lightly cross-linked, such as cross-links being formed by covalent or ionic bonds. The osmopolymers can be of plant, animal or synthetic origin. Hydrophilic polymers suitable for the present purpose include poly(hydroxyalkylmethacrylate) having a molecular weight of from 30,000 to 5,000,000; poly(vinylpyrrolidone) having molecular weight of from 10,000 to 360,000; anionic and cationic hydrogels; polyelectrolyte complexes; poly(vinyl alcohol) having a low acetate residual, cross-linked with glyoxal, formaldehyde, or glutaraldehyde and having a degree of polymerization from 200 to 30,000; a mixture of methyl cellulose, cross-linked agar and carboxymethyl cellulose; a water insoluble, water swellable copolymer produced by forming a dispersion of finely divided copolymer of maleic anhydride with styrene, ethylene, propylene, butylene or isobutylene cross-linked with from 0.0001 to about 0.5 moles of polyunsaturated cross-linking agent per mole of maleic anhydride in the copolymer; water swellable polymers of N-vinyl lactams, and the like.

Other osmopolymers operable as the expandable driving member 25 and initially surrounded by second wall section 12b comprise polymers that form hydrogels such as Carbopol® acidic carboxy polymers generally having a molecular weight of 450,000 to 4,000,000; the sodium salt of Carbopol® acidic carboxy polymers and other metal salts; Cyanamer® polyacrylamides; cross-linked water swellable indinemaleic anhydride polymers; Goodrite® polyacrylic acid having, but not limited to, a molecular weight of 80,000 to 200,000, and the sodium and other metal salts; Polyox® polyethylene oxide polymers having a molecular weight of 100,000 to 5,000,000; starch graft copolymers; AquaKeeps® acrylate polymers; diester cross-linked polyglucan, and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels, and in *Handbook of Common Polymers*, by Scott and Roff, published by the Chemical Rubber Company, CRC Press, Cleveland, Ohio.

The expandable driving member 25 in another preferred embodiment comprises an optional osmagent 26 dispersed therein. The osmagents are known also as osmotically effective solutes and they are also known as osmotically effective compounds. The osmotically effective compounds that can be used for the purpose of this invention include inorganic and organic compounds that exhibit an osmotic pressure gradient across a semipermeable wall. The osmotically effective compounds, along with the osmopolymers, imbibe fluid into the device thereby making available in situ fluid for imbibition by an osmopolymer to enhance its expansion. The osmotically effective compounds are used by mixing them with the osmopolymer, homogeneously or heterogeneously and then charging them into the delivery system. Osmotically effective solutes used for the former purpose include magnesium sulfate, magnesium chloride, sodium chloride, potassium chloride, potassium sulfate, sodium sulfate, lithium sulfate, potassium acid phosphate, d-mannitol, urea, inositol, magnesium succinate, tartaric acid, carbohydrates such as raffinos, sucrose, glucose, α-d-lactose monohydrate, mannitol, and mixtures thereof. The amount of osmagent in the blend with the osmopolymer usually is from 1% to 40%, or higher, with the total of all ingredients comprising the second composition equal to 100%.

The expandable driving member 25 in another preferred embodiment comprises an osmagent. The osmagent 26 can comprise a tablet, a layer, or osmagent 26 can be pressed into second wall section 12b. The osmagent can be in any suitable form such as particles, crystals, pellets, granules, and the like, when pressed into a tablet layer and into wall section 12b. Various osmotically effective solutes comprising magnesium sulfate, magnesium chloride, sodium chloride, lithium chloride, potassium sulfate, sodium carbonate, sodium sulfite, lithium sulfate, potassium chloride, calcium carbonate, potassium acid phosphate, sodium lactate, calcium lactate, mannitol, urea, inositol, magnesium succinate, tartaric acid, soluble carbohydrates such as raffinose, sucrose, glucose, lactose, mixtures thereof, and the like, can be used for this embodiment. The osmotic pressure of an osmagent, or an osmopolymer, can be measured using an osmometer. An osmometer used for the present measurements is identified as Model 320B, Vapor Pressure Osmometer, manufactured by the Hewlett Packard Co., Avondale, Pa. Osmagents and osmopolymers are known to the art in U.S. Pat. Nos. 4,327,725 and 4,612,008.

Layer 27, positioned between the beneficial agent composition and the expandable driving member is a means for (1) maintaining the separate identity of the beneficial agent composition and the driving member, for (2) transmitting the force generated by the driving member against the beneficial agent composition, and (3) for substantially restricting the passage of fluid between the beneficial agent composition and the driving member. Layer 27 comprises in one embodiment, an olefin, a vinyl, a condensation, an addition, an organosilicon, or an inorganic polymer. More specific polymer composition comprise high density polyethylene, high density polypropylene, polystyrene, polycarbonate, polyamide, elastomers, chlorinated rubber, styrene-butadiene rubber, chloroprene rubber, silicone, glass, and the like. In a presently preferred embodiment, layer 27 comprises a wax. More preferably, the waxes exhibit a melting point or a solidification point of about 45° C. or higher, usually 45° C. to 110° C. The waxes are selected from mineral, vegetable, plant, fish, animal, petroleum, and synthetic waxes. Representative waxes comprise a member selected from the group consisting of montan wax, ozokerite wax, carnuba wax, myricyl cerotate wax, beeswax, spermaceti wax, ceresini wax, gama wax, Japan wax, ouricury wax, ceresin wax, castor wax, Witco wax, polyethylene wax, and the like. Additionally, reinforcing agents such as Cabosil ® material can be incorporated into the wax for improving its structural integrity. In another manufacture, layer 27 can comprise a polymer elastomer possessing properties of low Shore A hardness, and Young's modulus, thermoplastic or thermoset, and essentially water impermeable.

The phrase, "exit means 13," as used herein, comprises means and methods suitable for the metered release of the beneficial agent 20 from compartment 18 of delivery system 10. The exit means 13 includes at least one passageway, orifice, or the like, through wall 12 for communicating with compartment 18. The expression, "at least one passageway," includes aperture, orifice, bore, pore, porous element through which the agent can migrate, hollow fiber, capillary tube, porous overlay, porous insert, and the like. The expression also includes material that erodes or is leached from the wall in the fluid environment of use to produce at least one passageway in dosage form 10. Representative material suitable for forming at least one passageway, or a multiplicity of passageways, include an erodible poly(glycolic) acid or poly(lactic) acid member in the wall; a gelatinous filament; poly(vinyl alcohol); leachable materials such as fluid removable pore forming polysaccharides, salts, or oxides, and the like. The expression includes structural characteristics that concentrate stress at a precise point in the wall so that only a small amount of force will induce breakage in the wall, yielding a passageway through the wall from compartment 18 to the outside of the device. A passageway or a plurality of passageways can be formed by leaching a material such as sorbitol, lactose and like water-soluble solids from the wall. The passageway can have any shape such as round, triangular, square, elliptical, and the like, for assisting in the metered release of beneficial agent from dosage form 10. Dosage form 10 can be constructed with one or more passageways in spaced apart relations or more than a single surface of a dosage form. Passageways and equipment for forming passageways are disclosed in U.S. Pat. Nos. 3,845,770; 3,916,899; 4,063,064 and 4,008,864. Passageways formed by leaching are disclosed in U.S. Pat. Nos. 4,200,098 and 4,285,987.

Delivery system 10 can be manufactured by standard manufacturing techniques. In one process, the first wall section 12a, and the second wall section 12b, independently are injection molded or extruded into the desired shape. Then, the first wall section 12a is filled with the beneficial agent composition comprising the beneficial agent, the pharmaceutically acceptable carrier, the pharmaceutically acceptable buffer and other components. Then, the second wall section 12b is filled with an expandable driving member and the layered partition next added thereto in layered arrangement. Optionally, the partition may be added to the first wall section 12a after filling with beneficial agent, in addition to, or instead of the partition added to second wall section 12b. Next, the two sections at their ends are slid together and they are optionally heat sealed, adhesive sealed, or solvent sealed, or ultrasonically sealed, or radiofrequency sealed, or spin welded, also known as friction heating to weld. Then, at least one passageway is drilled in the lead end of the manufactured assembly. Optionally, a passageway is drilled, or preformed in the wall and sealed with a break-off tab that is broken open, or cut open, or the like at the time of use to connect through the passageway the beneficial agent composition with the exterior of delivery system 10.

DETAILED DESCRIPTION OF EXAMPLES

The following examples are merely illustrative of the present invention and they should not be considered as limiting the scope of the invention in any way as these examples and other equivalents thereof will become apparent to those versed in the art in the light of the present disclosure, the drawings and the accompanying claims.

EXAMPLE 1

A delivery system manufactured in the shape of an implantable delivery device comprising a lead end with an exit passageway and a distant rear end is manufactured as follows: first, an expandable driving member is prepared by adding 9.5 liters of water and 500 g of polyvinyl pyrrolidone to a stainless steel container and the components mixed for 20 hours to obtain a smooth, binder solution. Next, 34.6 kg of sodium Carbomer ®, a sodium salt of polyacrylic acid polymer, is sized by forcing it through a 0.028 inch mesh screen in a fluid air mill set at 780-800 rpm speed. Then, 33 kg of the screened polymer is transferred to the granulator bowl of a fluid bed granulator and 6.6 liters of the binder solution is slowly sprayed onto the polymers in the granulator. The polymer granules are formed in this manner.

Next, 15 kg of sodium chloride is milled in a mill to a number 21 size mesh screen. Then, 31.32 kg of the granules of sodium Carbomer osmopolymer is mixed with 13.68 kg of the milled sodium chloride and the mix blended for about one hour. Then 455 gm of magnesium stearate is added and the ingredients blended for 10 minutes to produce a homogeneous expandable driving composition. The composition next is pressed into osmotically active tablets in a table press at a pressure of 500 lbs to produce a round, flat faced 30 mg tablet.

The semipermeable wall that surrounds a compartment for containing the osmotically active tablet is prepared as follows: first, 3.85 kg of cellulose acetate butyrate and 1.15 kg of tributyl citrate are dry mixed in a mixer for 5 minutes. This produced a polymer plasticizer blend of a 77/23 ratio for the rate controlling wall 12b. Next, a rubber mill is used to melt blend the blend, at a roller temperature of 70° C. The blend is transferred to the moving rollers of the mill and mixed for 3 minutes. Then, after all the materials are added to the mill, the temperature is raised to 90° C., followed by milling for 2 minutes, next the temperature is raised to 115° C. and followed by two more milling minutes, then the temperature is increased to 133° C. and followed by six minutes of milling the blend, and then the temperature is increased to 144° C. and followed by six minutes of milling the blend. After the rollers are cooled to 50° C., the blend is removed from the mill. The milled blend is cut into strips and passed through a grinder mill, and the resulting particles fed into an injection molder and molded into the semipermeable wall surrounding a compartment with an opened end for receiving an expandable driving member and for mating with the lead section of the delivery system.

Next, the lead, first wall section of the delivery system is prepared by adding 5 kg of polycarbonate to a hopper dryer and drying the polymer at 250° F. for 4 hours. Then, the dry polymer is fed into the hopper of an injection molder, where a single cavity hot tip mold is used to injection mold an impermeable wall surrounding a compartment with an open end for receiving components and for mating with the semipermeable wall member.

Next, the delivery system is assembled by first charging the subassembly semipermeable walled member with three osmotic tablets. Then, microcrystalline wax is melted and the molten wax poured on the top of the osmotic tablet to completely fill to the opened walled member. The charged subassembly is allowed to cool to room temperature.

Next, the delivery system subassembly comprising the substantially impermeable wall surrounding the compartment is filled with 340 mg of formulation at 40° C., wherein the formulation comprises 33 wt % (weight percent) porcine somatotropin, 4.57 wt % sodium phosphate monobasic, 28.1 wt % water, 33.3 wt % glycerol, and 0.67 wt % Tween-80. Then, the two subassemblies at their opened ends are joined by inserting partially the member comprising the osmotic tablets and the wax into the member comprising the formulation. Next, 4 drops of moisture-cured cyanoacrylic adhesive are dropped onto the remaining exposed surface, the members fully inserted and then twisted to effect a sealed delivery system. Finally, a 0.025 inch exit passageway is drilled into the member comprising the beneficial agent formulation to provide the manufactured delivery system.

EXAMPLE 2

A delivery system is manufactured as follows: first, a substantially fluid impermeable wall member is prepared by heating pellets of low density polyethylene followed by injection molding the hot polyethylene into a tube with an opened end and a closed end. The polyethylene is extruded neat, that is, free of any additions.

Next, a rate controlling wall, shaped as a tube with an opened end and a closed end, is prepared from a wall forming composition comprising 28 g of cellulose acetate butyrate, 10 g of tributyl citrate and 12 g of polymethyl methacrylate. The rate controlling wall is prepared by slowly adding 12 g polymethyl methacrylate to a heated mixer, 170° C., and mixed for about 5 minutes to allow the polymer crystals to fuse together. Next, several drops of the tributyl citrate plasticizer are added to the mixer. Then, about 5 g of the tributyl citrate is added to 28 g of cellulose acetate butyrate and the two ingedients mixed thoroughly into a homogeneous mixture. Next, the remainder of the tributyl citrate is added slowly to the polymethyl methacrylate, tributyl citrate in the mixer and the temperature of the mixer is lowered to 135° C. Next, the cellulose acetate butyrate, tributyl citrate blend is added to the mixer and the temperature raised to 190° C., to uniformly melt the cellulose acetate butyrate. After 5 minutes at this temperature, the temperature of the mixer is lowered to 100° C. and the mixing continued for 5 additional minutes. The mixer was cooled to room temperature and the rate controlled wall forming composition cut into small pieces.

Then, the cut wall forming composition is fed into a turning extruder, about 8 rpm, and forced through the core passageway of the extruder. The composition melts at the temperature of the extruder and its die, about 140° C. to 150° C. The resultant rate controlling wall tubing measured about 0.176 inch outer diameter, 0.156 inch inside diameter, with a wall thickness of about 10 mils (0.256 mm). Then, one end of the tube is sealed with a cellulose acetate plug with a drop of adhesive to provide a rate controlling wall that surrounds a compartment with an opened end and a closed end.

Next, a driving member composition is prepared from a composition comprising 670 g of sodium Carbomer ®, the sodium salt of polyacrylic acid, 290 g of sodium chloride, 40 g of polyvinyl pyrrolidone and 10 g of magnesium stearate by wet granulating with denatured ethanol in a 90:10 ratio in deionized water. Approximately 700 ml of granulation solvent is used for the wet granulation. Next, the wet granulation is passed through a ten mesh screen and placed in a 50° C. oven and dried over night. After drying the granulation is removed from the oven and allowed to hydrate to approximately 9.3% water content. The gradulation is passed again through a 10 mesh screen. After granulation 10.1 g of magnesium stearate is added and all the ingredients mixed for about 5 minutes. The resulting granulation is ready for use in the delivery device.

Then, 96 mg of the driving member composition is weighted and compressed in a Carver ® laboratory press. The composition is pressed with a 5/32 inch round die and punched with one end flat and the other end concave. The compressed composition is inserted into one end of the rate controlling member with the dome flush with the end of the wall.

Next, about 100 g of microcrystalline wax that forms the interface layer between the driving member composition and the beneficial agent composition is melted in a 72° C. forced air oven to a molten state. Then, 10 cc of a glass syringe is filled with the molten wax and a layer 1.25 cm is deposited at the interface of the driving member composition. The wax is allowed to cool to room temperature.

Next, the wall member comprising the substantially impermeable polymer is filled with a beneficial agent formulation. The formulation is prepared by adding 20.58 g of glycerol into a beaker and 0.42 g of porcine gelatin added to the glycerol. The two ingredients are stirred for about ½ hour at room temperature. Then, an amino acid and, in another manufacture, a surfactant is added and the mixture heated at 60°-70° with constant stirring to yield a uniform blend. The heating and mixing are continued for about ½ hour. Finally, the mixture is allowed to cool to room temperature.

Then, 13.3 g of the freshly prepared composition is added to 5.7 g of porcine somatotropin and blended with a spatula. The somatotropin hormone is added in small increments and blended to yield the hormone formulation. The hormone formulation is injected into the receiving housing to fill the member. Next, the first substantially fluid impermeable member and the second rate controlling member are brought into contact at their open ends and heat sealed to form a closed compartment. Finally, an exit passageway is drilled through the wall for connecting the exterior of the delivery device with the beneficial hormone formulation for its delivery to an animal.

EXAMPLE 3

A delivery system for delivering a beneficial agent is prepared comprising (a) a first cylinder shaped housing member comprising a nylon wall that exhibits a low permeability to fluid and surrounds an internal reservoir; and, a second cylinder shaped housing member comprising a cellulose acetate having an acetyl content of 38.3% wall that surrounds an internal reservoir. The open ends of each member are joined into an integral delivery system. The union is effected by enlarging the end of the first member for slidably, receiving the end of the second member in mated relation to form an essentially fluid tight union. In another embodiment, at least one of the ends of the first member or the second member is made smaller than the other end and the smaller end placed in the non-enlarged end to form a closed delivery system. The respective members are filled prior to telescoping them lengthwise into a manufactured deliverd system. An exit passageway is laser drilled through the wall of the first member for delivering a beneficial agent formulation from the delivery system.

The first housing member, in one manufacture, is charged with a dispensable formulation comprising a protein such as a hormone like insulin, a polyol such as glycerol that increases its solubility in water without affecting its biological activity, buffered sodium acetate water and polysorbate-80, a sorbitan monooleate polyoxyethylene. The second housing member comprises a first layer of the sodium salt of polyacrylic acid, a middle layer of sodium chloride, a third layer of the sodium salt of polyacrylic acid, and a layer of wax at the interface between the beneficial hormone formulation and the layer of the sodium salt of polyacrylic polymer.

EXAMPLE 4

The procedure of Example 3 is followed with the conditions as set forth, except that in this example the first housing member formulation comprises bovine somatotropin dissolved in buffered tris(hydroxymethyl) amino solution comprising the polyols glycerol and erythriol, and the surfactant sodium lauryl sulfate; and the second housing member comprises a first compressed layer of the sodium salt of polyacrylic acid, a second compressed layer of the sodium salt of polyacrylic acid, a third compressed layer of the sodium salt of polyacrylic acid, and a layer of the polyolefin polyethylene.

EXAMPLE 5

An embodiment of the invention pertains to a method for delivering a beneficial agent such as a drug to an animal. The method comprises implanting a delivery system, shaped, sized and adapted as an implant into an animal, such as a muscle thereof. The method comprises the steps of: (A) admitting into an animal a delivery system comprising: (1) a housing comprising an internal lumen, which housing comprises: (2) a first wall section comprising a composition that limits the passage of fluid into the lumen; (3) a second wall section comprising a composition that permits the passage of fluid into the lumen; (4) a beneficial agent formulation in the lumen comprising the first wall section; (5) an expandable driving composition in the lumen comprising the second wall section; (6) a layer comprising a composition substantially impermeable to the passage of fluid interposed between the beneficial agent formulation and the driving means; and (7) at least one orifice in the device communicating with the lumen; (B) imbibing fluid through the wall for causing the driving means to expand and push against the beneficial agent formulation; and (C) delivering the beneficial agent formulation from the delivery system by the expandable means continuously expanding at a controlled rate thereby causing the beneficial agent formulation to be delivered in an effective amount through the orifice to the animal over a prolonged period of time.

The novel devices of this invention use means for the obtainment of precise release rates in the environment of use while simultaneously maintaining the integrity of the device. While there has been described and pointed out features of the invention as applied to presently preferred embodiments, those skilled in the art will appreciate that various modifications, changes, additions and omissions in the devices illustrated and described can be made without departing from the spirit of the invention.

We claim:

1. A method for delivering a somatotropin agent to an animal, wherein the method comprises:
    (a) admitting into the animal a dispenser comprising:
        (1) a wall that surrounds an internal lumen, said wall comprising a first section that substantially limits the passage of fluid through the wall and a second section that permits the passge of fluid through the wall and comprises a pair of ends with one end inside the other end and held together by a manufacture selected from the group consisting of bonding, welding and friction as a means for replacing one of the sections during use of the dispenser;
        (2) a somatotropin composition comprising 5 nanograms to 20 grams in the lumen wherein the first section of the wall limits the passage of fluid for substantially protecting the somatotropin from the fluid present in the animal;
        (3) an osmopolymer composition comprising an expandable hydrogel in the lumen initially present in the second section of the wall that permits the passage of fluid;
        (4) at least one exit passageway in the wall for delivering the somatotropin from the dispenser; and,
    (b) delivering to somatotropin to the animal by the osmopolymer hydrogel imbibing fluid and thereby occupying space in the lumen, for pushing the somatotropin through the passageway to the animal.

2. The method for delivering the somatotropin to the animal according to claim 1, wherein the animal is a pig.

3. The method for delivering the somatotropin to the animal according to claim 1, wherein the somatotropin is porcine somatotropin.

4. The method for delivering the somatotropin to the animal according to claim 1, wherein a partition is between the somatotropin and the osmagent.

5. A dispenser for delivering a beneficial agent to an animal, the dispenser comprising: a wall surrounding an internal lumen, said wall comprising a first section that substantially limits the passage of fluid through the wall and a second section that permits the passage of fluid through the wall; said wall comprising a pair of ends with one end placed inside the other end, and held together by a manufacture selected from the group consisting of bonding, welding and friction as a means for releasably replacing one of the sections during use of the dispenser; a beneficial agent formulation in the lumen comprising a pharmaceutically acceptable carrier and from 5 nanograms to 20 grams of a beneficial agent in the first section for substantially protecting the beneficial agent from an exterior fluid present in the animal; an osmotic composition comprising 100% in the lumen in the second section, the osmotic composition comprising an osmopolymer for imbibing fluid for increasing its polymeric volume for displacing the beneficial agent formulation from the first section; and at least one exit passageway in the dispenser for delivering the beneficial agent to the animal.

* * * * *